(12) United States Patent
Guru et al.

(10) Patent No.: US 11,051,901 B2
(45) Date of Patent: Jul. 6, 2021

(54) MEDICAL INSTRUMENT CART

(71) Applicants: Health Research, Inc., Buffalo, NY (US); The Research Foundation for The State University of New York, Amherst, NY (US)

(72) Inventors: Khurshid Guru, East Amherst, NY (US); Albert Titus, Buffalo, NY (US); Kyle Weeks, Lockport, NY (US)

(73) Assignees: Health Research, Inc., Buffalo, NY (US); The Research Foundation for the State University of New York, Amherst, NY (US)

( * ) Notice: Subject to any disclaimer, the term of this patent is extended or adjusted under 35 U.S.C. 154(b) by 0 days.

(21) Appl. No.: 16/468,223

(22) PCT Filed: Dec. 8, 2017

(86) PCT No.: PCT/US2017/065325
§ 371 (c)(1),
(2) Date: Jun. 10, 2019

(87) PCT Pub. No.: WO2018/107035
PCT Pub. Date: Jun. 14, 2018

(65) Prior Publication Data
US 2019/0328477 A1    Oct. 31, 2019

Related U.S. Application Data

(60) Provisional application No. 62/431,423, filed on Dec. 8, 2016.

(51) Int. Cl.
*A61B 50/13*        (2016.01)
*A61G 12/00*        (2006.01)
*A61L 2/26*         (2006.01)
*A61B 34/30*        (2016.01)
*A61B 90/90*        (2016.01)

(52) U.S. Cl.
CPC ............ *A61B 50/13* (2016.02); *A61G 12/001* (2013.01); *A61L 2/26* (2013.01); *A61B 34/30* (2016.02); *A61B 90/90* (2016.02); *A61L 2202/16* (2013.01); *A61L 2202/182* (2013.01); *A61L 2202/24* (2013.01)

(58) Field of Classification Search
CPC ......... A61B 50/13; A61B 34/30; A61B 90/90; A61G 12/001; A61L 2/26; A61L 2202/16; A61L 2202/182; A61L 2202/24
USPC ................................................. 700/231–244
See application file for complete search history.

(56) References Cited

U.S. PATENT DOCUMENTS 4,695,954 A      9/1987  Rose et al.
4,811,764 A  *   3/1989  McLaughlin ......... A61J 7/0084
                                                   141/104

(Continued)

*Primary Examiner* — Michael Collins
(74) *Attorney, Agent, or Firm* — Hodgson Russ LLP

(57) ABSTRACT

A cart for dispensing, storing, and tracking medical instruments is provided. The cart has a housing, a first motor, a second motor, one or more trays, and a processor. The trays hold one or more medical instruments, and have a door and door opening assembly. The processor is in communication with the motors for rotating the housing and opening the doors. The processor has a storage medium for storing the cart's instrument dispensing history. The processor also has a user interface for capturing user input.

12 Claims, 11 Drawing Sheets

(56) References Cited

U.S. PATENT DOCUMENTS

| | | | |
|---|---|---|---|
| 4,847,764 | A | 7/1989 | Halvorson |
| 5,014,875 | A * | 5/1991 | McLaughlin ....... G07F 17/0092 |
| | | | 221/122 |
| 5,152,422 | A * | 10/1992 | Springer ............... A61J 7/0084 |
| | | | 221/113 |
| 5,745,366 | A | 4/1998 | Higham et al. |
| 6,604,019 | B2 * | 8/2003 | Ahlin .................. G07F 17/0092 |
| | | | 700/231 |
| 7,952,315 | B2 * | 5/2011 | Park, IV ................. G07F 11/54 |
| | | | 318/578 |
| 2002/0173875 | A1 | 11/2002 | Wallace et al. |
| 2004/0046020 | A1 | 3/2004 | Andreasson et al. |
| 2007/0078562 | A1 | 4/2007 | Park, IV |
| 2008/0316045 | A1 | 12/2008 | Sriharto et al. |
| 2010/0152885 | A1 * | 6/2010 | Regan .................... G01N 35/04 |
| | | | 700/217 |
| 2011/0172815 | A1 | 7/2011 | Kim |
| 2012/0203377 | A1 | 8/2012 | Paydar et al. |
| 2013/0253700 | A1 | 9/2013 | Carson et al. |

\* cited by examiner

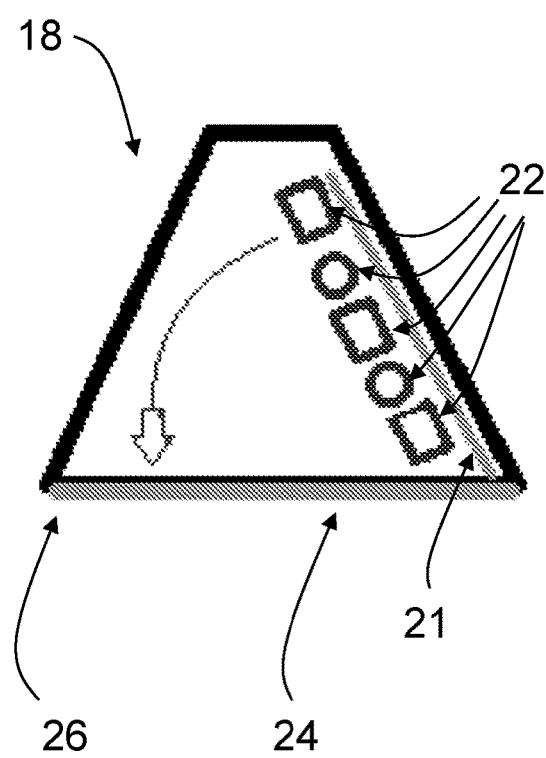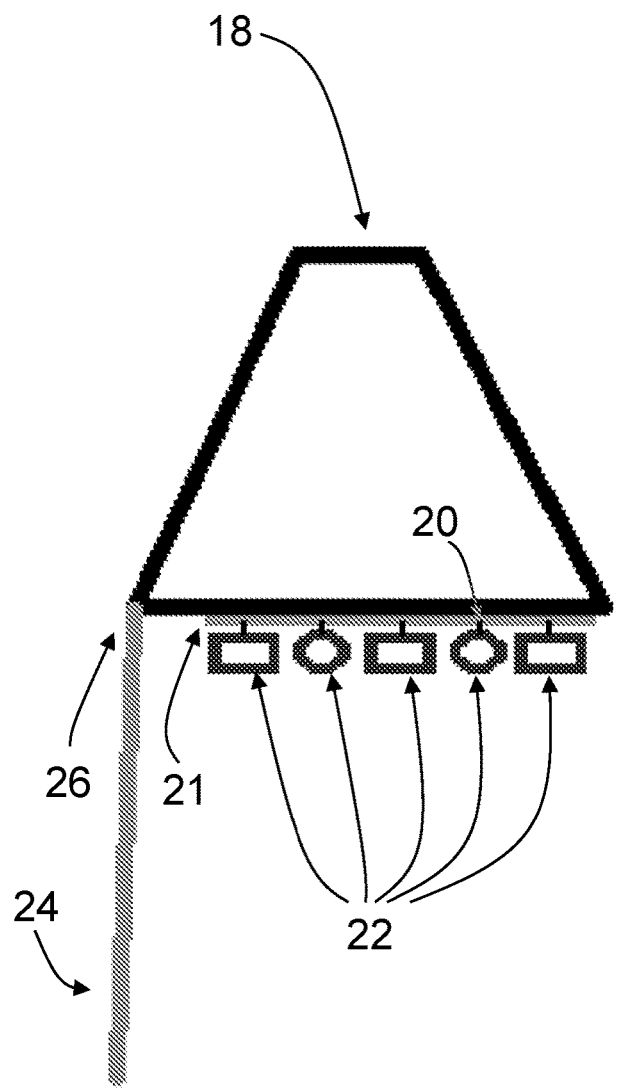
Fig. 11a
Fig. 11b

MEDICAL INSTRUMENT CART

CROSS-REFERENCE TO RELATED APPLICATIONS

This application claims priority to U.S. Provisional Application No. 62/431,423, filed on Dec. 8, 2016, the disclosure of which is incorporated herein by reference.

FIELD OF THE DISCLOSURE

This disclosure relates to an operating room cart for sorting, dispensing, and tracking medical instruments.

BACKGROUND OF THE DISCLOSURE

The operating room ("OR") is a complex work environment. There are many people working together to complete a complicated procedure. Many specialized tools may be used, and everything related to the procedure must be sterile. There is significant effort made to streamline the surgical process and to reduce the potential for mistakes, as mistakes can be costly. One area in particular that has the potential for improvement is the process of delivering instruments into the OR and the subsequent setting up of the "back table" with the instruments. As an example, instrument trays (containers for sterilization and storage of instruments) may enter the OR with broken or missing instruments. In another aspect, one study found that 16% of trays brought into the OR had either one or zero instruments used. All of the instruments brought into an OR and exposed to the air have to be cleaned and sterilized before they can be reused. Cleaning unused tools results in wasted time and resources, and can lead to delays in surgery and increased risk to patients. There are also ergonomic risks associated with setup of instruments for surgery, such as, for example, handing instruments to the surgeon or physician's assistant, changing instruments attached to a surgical robot, and cleanup of instruments after surgery. There are also issues in the OR related to tracking instruments (e.g., counting instruments), which, in an extreme case, may result in an instrument being left inside the patient (retained instruments).

Accordingly, there is a critical, long-felt need for systems and methods to streamline surgical processes, to increase the efficiency of ORs and reduce the risks for mistakes.

BRIEF SUMMARY OF THE DISCLOSURE

A cart for dispensing, storing, and tracking medical instruments is provided. Use of this cart will improve efficiency in operating room settings by desterilizing only the medical instruments required for the current procedure.

In an embodiment, the cart comprises a housing, a first motor, a second motor, one or more trays disposed within the cart, and a processor. The housing may have a longitudinal axis. The first motor is configured to rotate the housing about the longitudinal axis. Each tray is configured to hold one or more retainers. The retainers are configured hold one or more medical instruments. Each tray also has a door and a door opening assembly configured to open the door.

The processor is in electronic communication with the first motor for rotating the housing about the longitudinal axis and the door opening assemblies for opening the doors. The processor has a storage medium for storing the cart's instrument dispensing history. The processor also has a user interface for capturing user input.

Prior to a procedure, the cart is loaded with required instruments along with necessary backups. Once loaded, the cart keeps the instruments sterile until they are selected and opened by the nurse. During the procedure, a user selects a required instrument using the user interface. The first motor rotates the housing such that the tray containing the instrument is facing the user. The door assembly opens the door of the tray. The retainer may have a motor configured to move the tray towards the user. In either case, the user may then retrieve the instrument from the cart. The processor records the instrument retrieved on the storage medium. The cart therefore keeps all unused instruments sterile during the procedure, and records all used instruments as unsterile.

In some embodiments, the design of the cart is based on a need to house tools used with the da Vinci Surgical System by Intuitive Surgical. For a robotic surgery, a combination of open instruments (those used in open surgery), laparoscopic instruments, and robotic instruments may be used.

DESCRIPTION OF THE DRAWINGS

For a fuller understanding of the nature and objects of the disclosure, reference should be made to the following detailed description taken in conjunction with the accompanying drawings, in which:

FIG. 11a is a line drawing of another embodiment of a tray, closed door, and medical instruments; and FIG. 11b is a line drawing of another embodiment of a tray, open door, and medical instruments moved outside of the tray.

DETAILED DESCRIPTION OF THE DISCLOSURE

Figure 1:
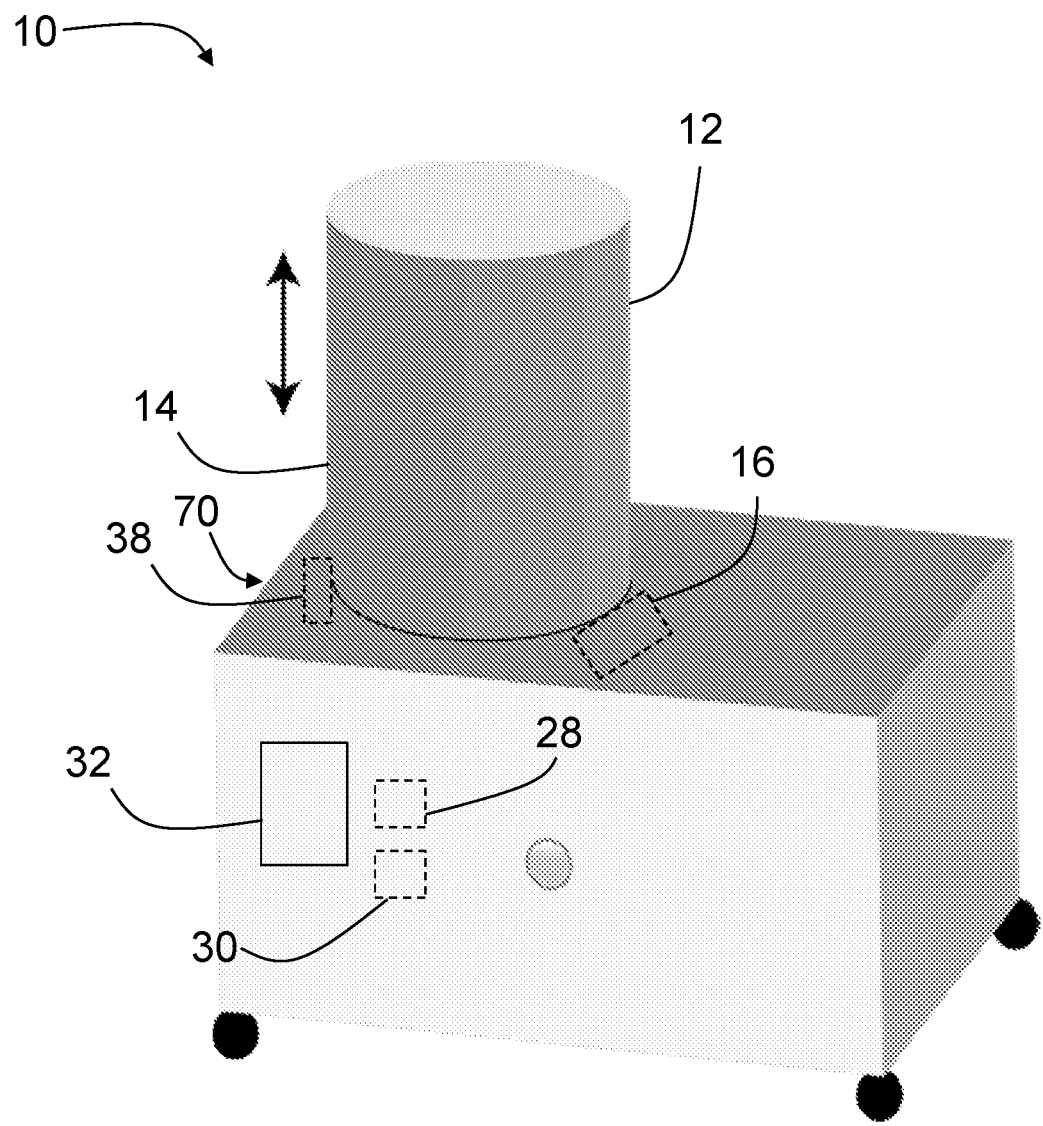
FIG. 1 is a simplified perspective diagram of a cart according to an embodiment of the present disclosure.
Figure 2:
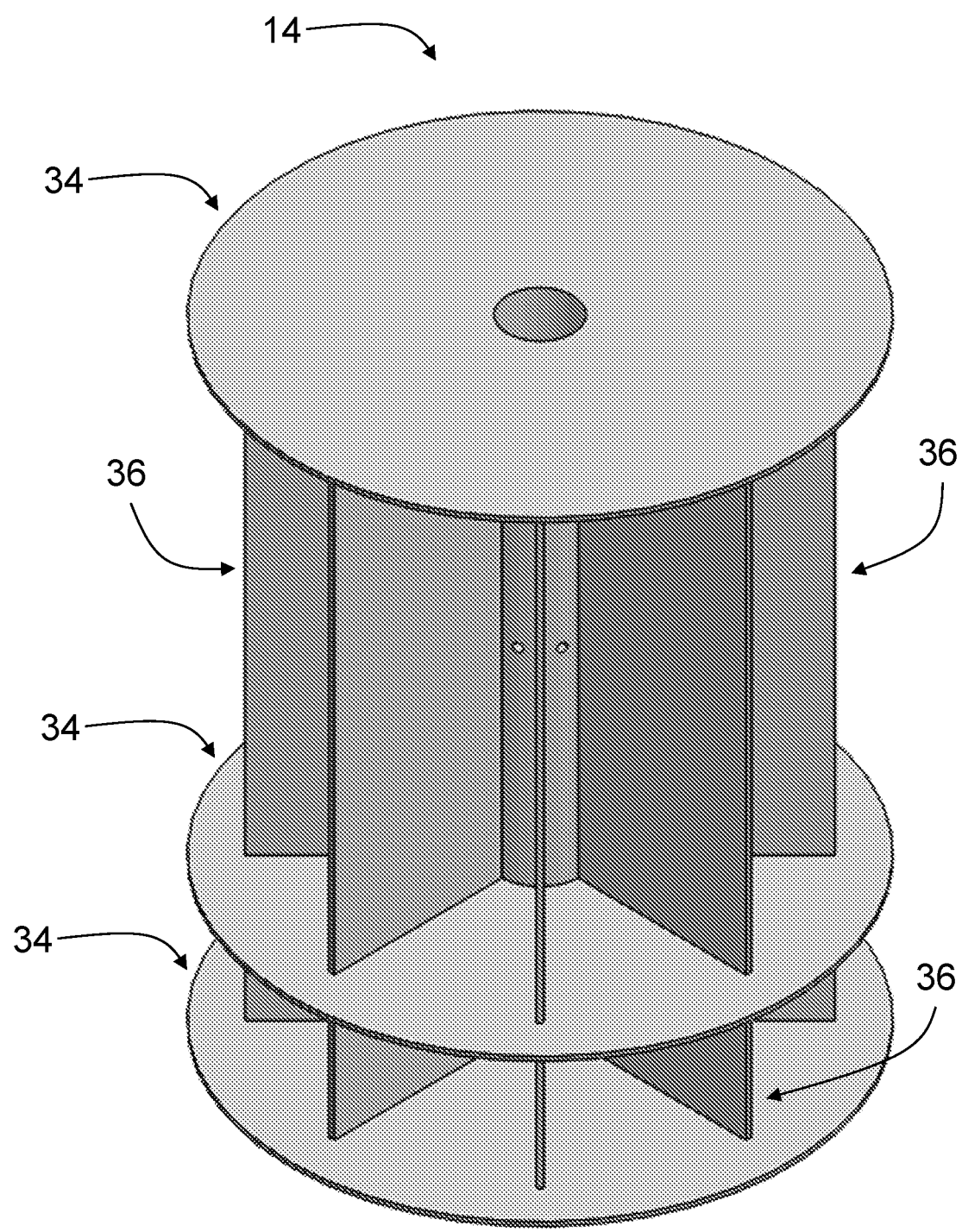
FIG. 2 is a perspective view of an embodiment of a housing with shelves.
Figure 3:
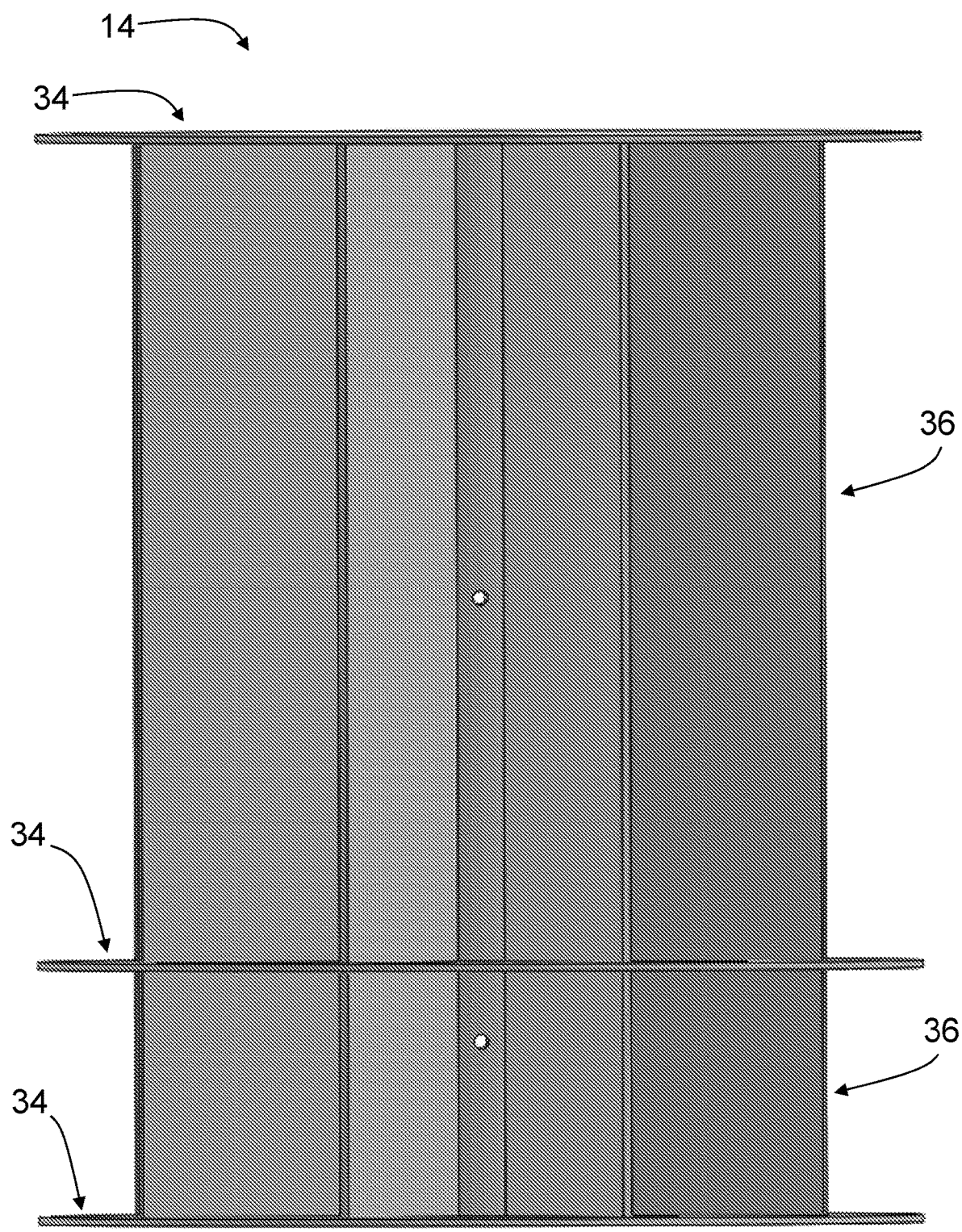
FIG. 3 is a side view of the embodiment of the housing from FIG. 2.

With reference to FIGS. 1-2, in an aspect of the present disclosure, a cart 10 for medical instruments 22 is provided. Such a cart 10 may be useful to, for example, store, dispense, and track medical instruments. The cart 10 comprises a housing 14 having a longitudinal axis 1 about which the housing 14 can be rotated. In some embodiments, the housing 14 is generally cylindrical and the longitudinal axis runs through the center of the cylinder (i.e., at the center of a circular cross-section of the cylinder). The housing 14 may be made from any suitable material as will be apparent to one having skill in the art in light of the present disclosure. For example, the housing 14 may be made from a plastic, such as, for example, Nylon or polycarbonate.

The cart 10 has a first motor 16 configured to rotate the housing 14 about the longitudinal axis. A processor 28 is operably connected to the first motor 16, such that, for example, the first motor 16 may be activated by the processor 28 to rotate the housing 14. The first motor 16 may be, for example, a stepper motor or a servo motor. In some embodiments, the first motor 16 may be adjacent to the housing 14 and configured to cooperate with a periphery of the housing 14 to cause rotation. In other embodiments, the motor may be positioned at or near the longitudinal axis of the housing 14 to rotate an axle to rotate the housing 14. Other options for positioning the first motor 16 will be apparent to one with skill in the art in light of present disclosure.

Figure 4:
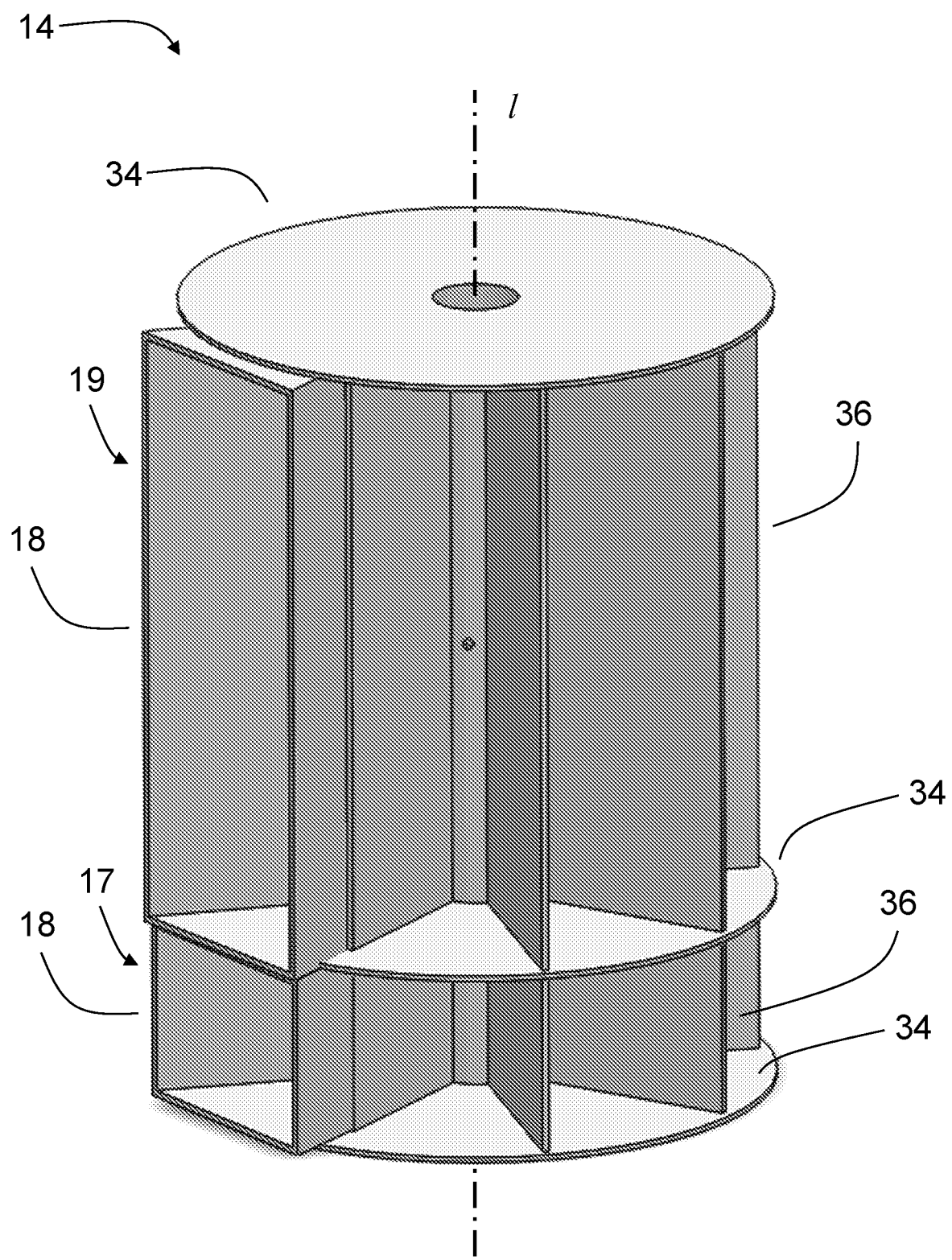
FIG. 4 is a perspective view of an embodiment of the housing with two trays.
Figure 5:
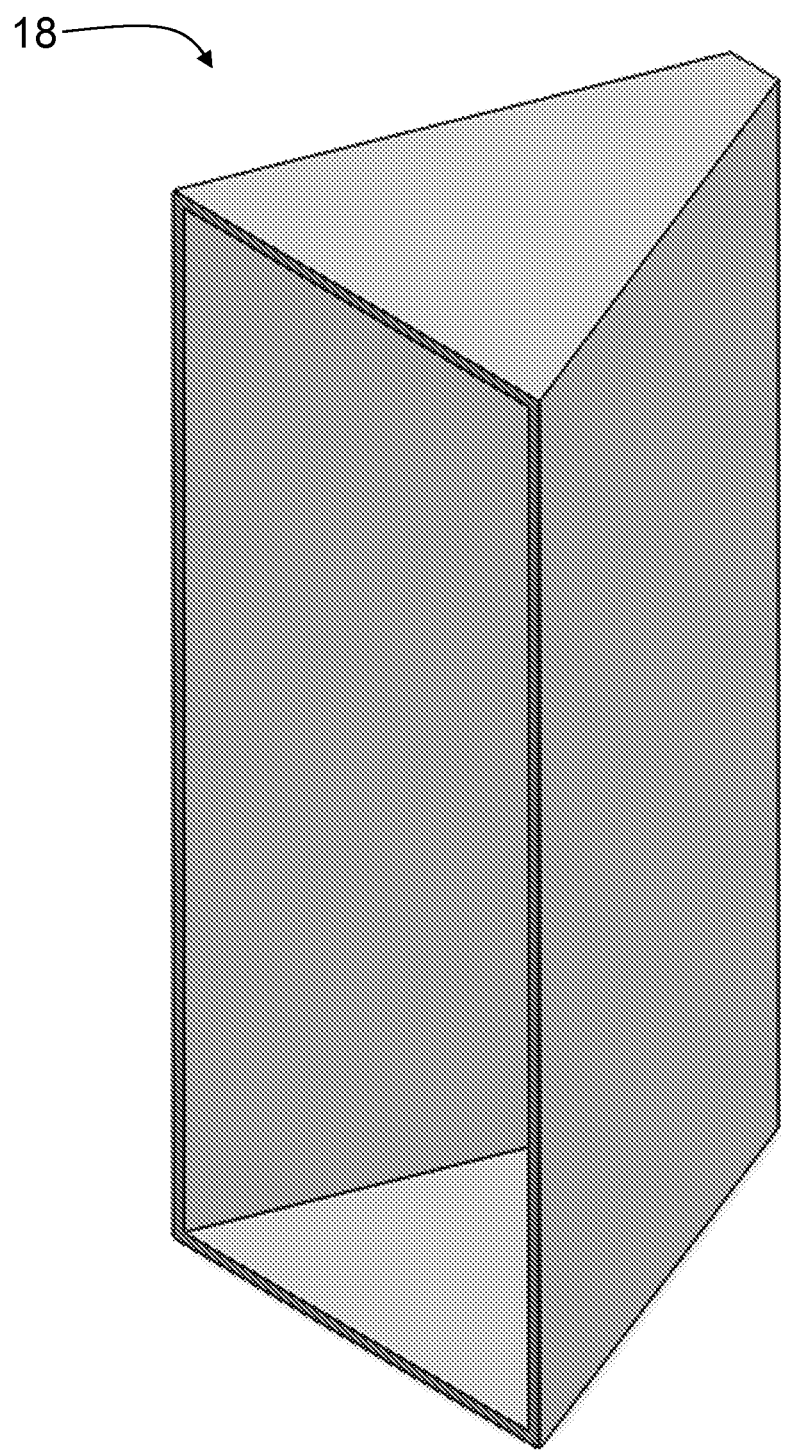
FIG. 5 is a perspective view of an embodiment of a tray.
Figure 6:
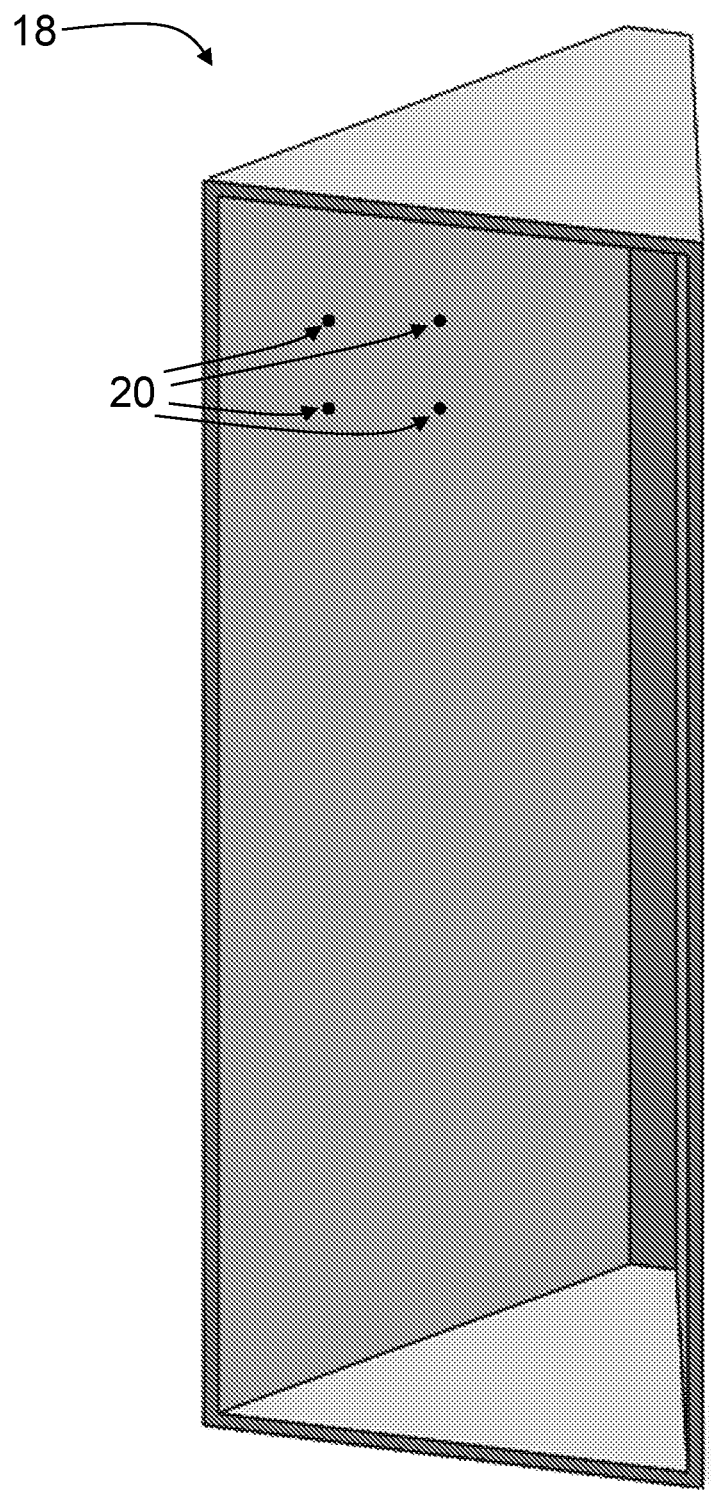
FIG. 6 is different perspective view of the embodiment of the tray from FIG. 5.
Figure 7:
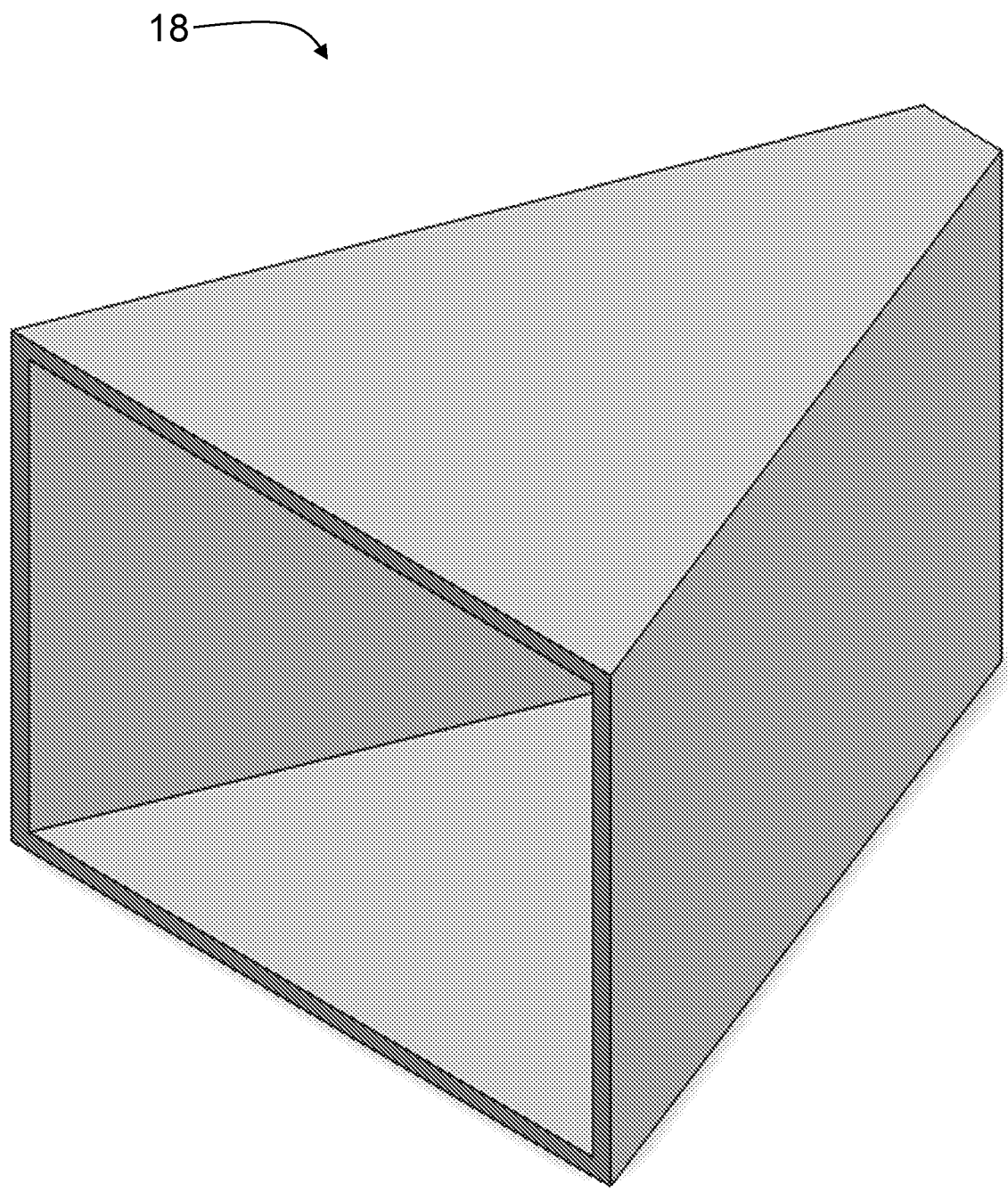
FIG. 7 is a perspective view of another embodiment of a tray.
Figure 8:
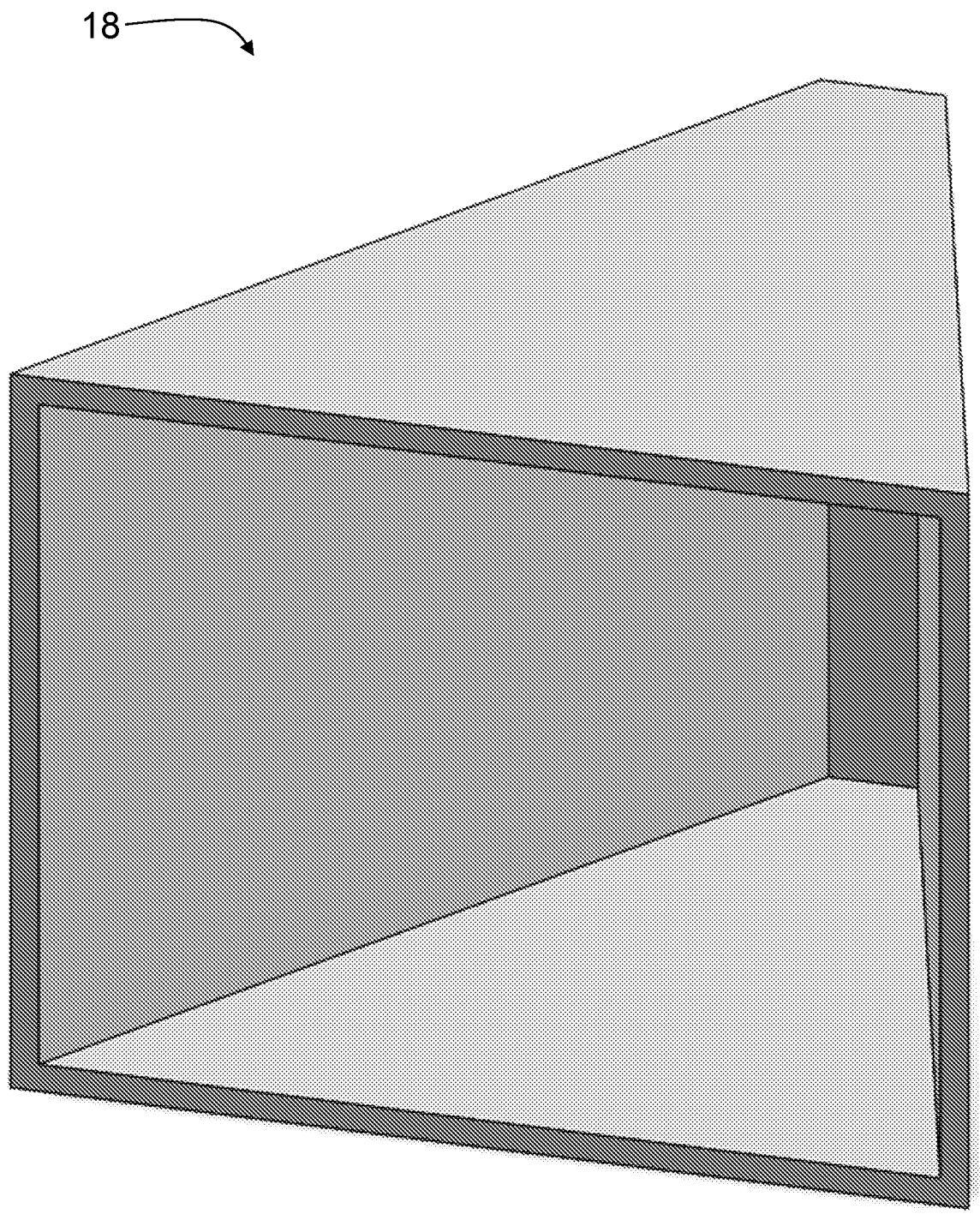
FIG. 8 is a different perspective view of the embodiment of the tray from FIG. 7.
Figure 9A:
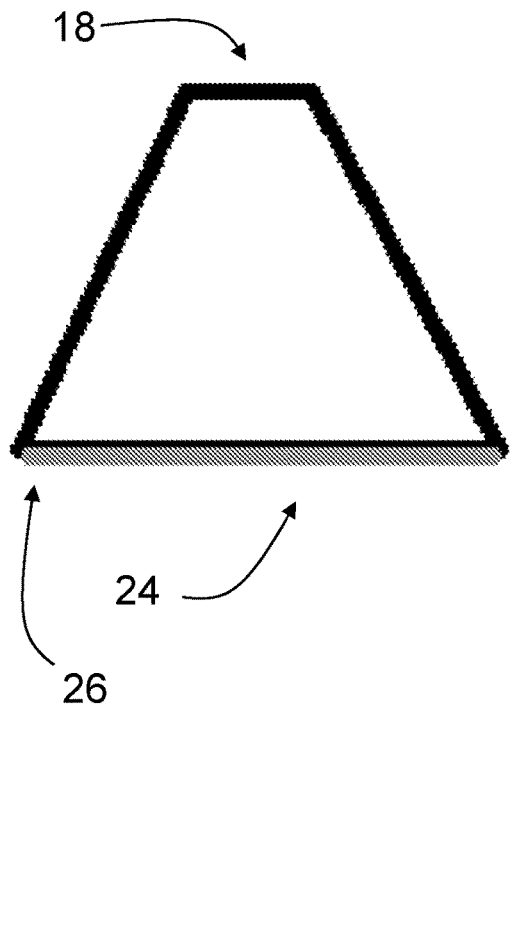
FIG. 9a is a line drawing of an embodiment of a tray with a closed door.
Figure 9B:
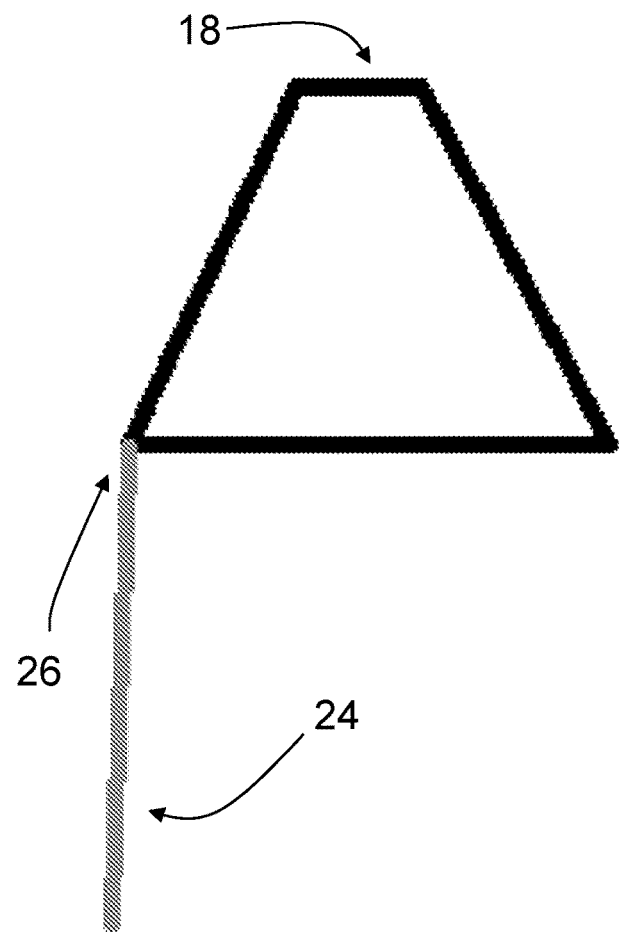
FIG. 9b is a line drawing of an embodiment of a tray with an opened door.

As shown in FIG. 4, the cart 10 also includes one or more trays 18 removably disposed in the housing 14. Each tray 18 includes a door 24 (FIG. 9a), configured to enclose an interior volume of the corresponding tray 18. In some embodiments, each door 24 is configured to cooperate with the corresponding tray 18 to seal the interior volume of the tray 18 such that once the interior volume and its contents are sterilized, they remain sterile until the door 24 is opened.

The outer surfaces of the trays 18 and/or doors 24 may not be sterile. As such it may be advantageous to provide the ability for a user to open each door 24 without the use of their hands. In this way, the user's hands need not come into contact with contaminates that may be on the tray 18 and/or door 24. As such, embodiments of a cart 10 may comprise an actuator 26 configured to open each door 24. The actuator 26 may make up a part of a tray 18 such that each tray 18 has a corresponding door actuator 26. In other embodiments, the door actuator 26 may be a part of the housing 14 such that the door actuator 26 can cooperate with each door 24 in turn as the housing 14 is rotated about the longitudinal axis 1. In some embodiments, the actuator 26 is a mechanical linkage or a portion of a mechanical linkage. In this way, the actuator 26 is actuated by manipulation of the linkage by the user. For example, the door actuator 26 may be part of a mechanical assembly having a foot pedal such that the door 24 may be opened by the user depressing the foot petal. As will be apparent, such a mechanical assembly may also include linkages and springs such that the components can return to an initial position after being actuated. In other embodiments, the actuator 26 is an electric actuator, such as, for example, an electric motor, a solenoid, etc.

Figure 10A:
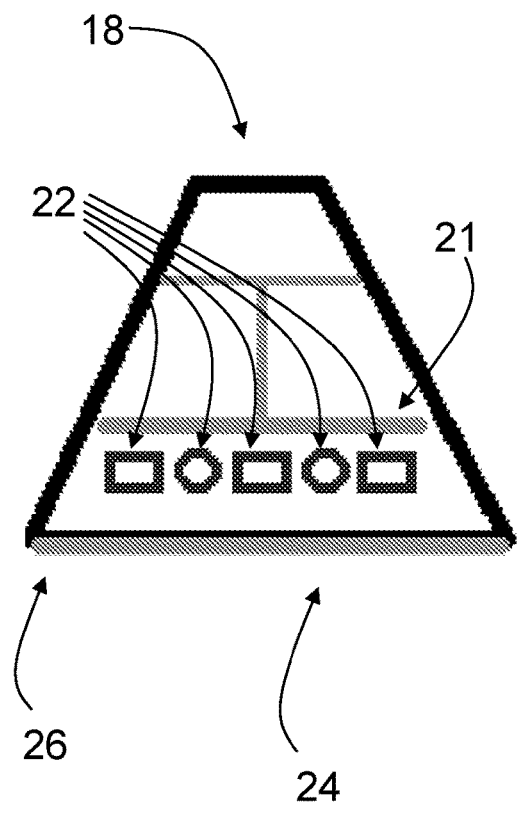
FIG. 10a is a line drawing of an embodiment of a tray, closed door, and medical instruments.
Figure 10B:
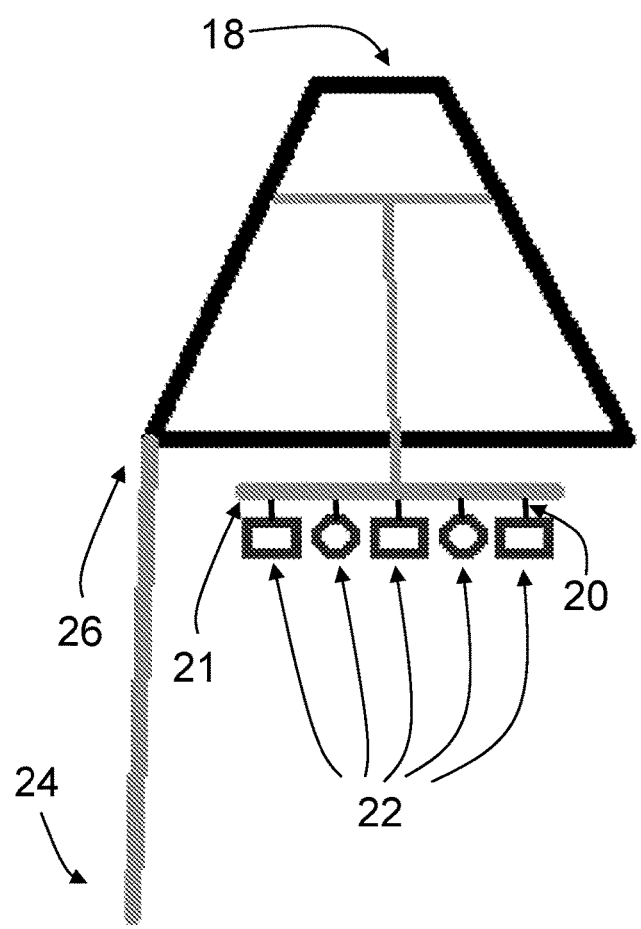
FIG. 10b is a line drawing of an embodiment of a tray, open door, and medical instruments moved outside of the tray.

Each tray 18 of the one or more trays has one or more retainers 20 (see, e.g., FIGS. 10b and 11b) configured to hold a medical instrument 22. The retainers 20 may be, for example, brackets, clips, hangers, and/or any other such suitable retention device as is known in the art. The medical instruments 22 held by the retainers 20 may include robotic hooks, robotic needle drivers, robotic bipolars, robotic scissors, laparoscopic suctions, laparoscopic needle drivers, laparoscopic graspers, laparoscopic hooks, metallic ports, and other various open instruments. Spares of the robotic instruments may also be held. The trays 18 may be of any size suitable for the particular application. The trays 18 may be of differing sizes. For example, in some embodiments, the trays 18 may be two different sizes—a long tray 19 and a short tray 17 (as shown in FIG. 4) used to accommodate (e.g., store) instruments of corresponding sizes. The trays 18 and/or retainers 20 may be configured to store instruments in any orientation. For example, in some embodiments, long trays 19 and the associated retainers 20 may be configured to hold instruments in a vertical orientation.

The processor 28 of the cart 10 may be programmed to receive a request for a medical instrument 22. The processor 28 operates the first motor 16 causing the motor to rotate the housing until a tray 18 containing the requested medical instrument is moved to a working position (i.e., a position where the door 24 may be opened for retrieval of the instrument by the user). The processor 28 may record a use of the requested instrument. For example, the cart 10 may have a storage medium for recording the usage information. In other embodiments, other usage information is recorded. For example, the occasion of a door 24 opening may be recorded because such an occurrence will desterilize the tray 18 and its contents.

The trays 18 may be configured such that the doors 24 are arranged around the periphery of the housing 14. In this way, the housing 14 can be rotated to move a desired tray 18 to a working position. The working position may be a position where the user can easily access the tray and the instruments within. In some embodiments, the working position may be accessible by a robot for automated retrieval of instruments. In such an embodiment, the robot may also interface with the processor to integrate the retrieval of instruments. In embodiments where the housing 14 is generally cylindrical, the trays 18 may have a trapezoidal shape such that they may be arranged with the doors around the periphery of the housing.

In some embodiments, the cart 10 may further comprise a lift motor 38 configured to translate the housing 14 along the longitudinal axis. The lift motor 38 may be used to lower the housing 14 into, and raise the housing 14 from, an enclosure 70 of the cart 10. In this way, the housing 14 is able to descend into the enclosure 70, which has the benefits of limiting the exposure of the trays 18 to the air to limit airborne pathogens, and also making transportation of the cart 10 easier.

The one or more trays 18 may be removable. In some embodiments, the trays 18 are autoclavable. As such, the trays 18 may be configured to be penetrable by steam while in an autoclave, and the contents of the tray 18 are able to dry during a drying cycle of the autoclave. The trays 18 may be made from any suitable material or materials, for example, aluminum. The trays 18 may have handles, and, in some embodiments, the trays 18 are configured to be stackable.

In one embodiment, the retainers 20 may be configured to move relative to the tray 18. For example, each tray may include a moveable platform 21 to which the one or more retainers are affixed (see, e.g., FIGS. 10b, 11b). The moveable platform may be then be configured to move any instruments held by the retainer(s) to a user position when the door of the respective tray is opened, for more convenient access by the user. The platform may move by rotating from a secure position to the user position (see, e.g., FIGS. 11a, 11b). In other embodiments, the platform may be configured to translate to a user position, for example, using a scissor-type or other mechanism.

The trays may incorporate sensors and/or other electronics for tracking instruments. For example, the trays may incorporate one or more sensors to detect the presence of absence of an instrument in a retainer. In this way, the sensor may send a signal to the processor, for example, to indicate that a tool has been removed. In another example, sensors may be able to interrogate the tools in the tray retainers to inventory the available tools. In this way, when a request for an instrument is received by the processor, an up-to-date inventory is available for the processor to use in providing the tool (e.g., rotating the housing and actuating the door on the appropriate tray). In yet another example, a sensor may detect when the door of the tray is opened, and optionally signal the processor accordingly. Accordingly, the tray 18 can be coded to "know" which instruments it contains, and to "know" if the door 24 has been opened.

In some embodiments of the presently-disclosed cart, the housing 14 further comprises one or more shelves 34 disposed within the housing 14. In such embodiments, the trays 18 are configured to fit within the shelves 34. In some embodiments, the housing 14 further comprises one or more vertical dividers 36 disposed in the housing 14 to separate the trays.

FIG. 2 shows an embodiment of the housing 14 wherein the housing 14 is substantially cylindrical and has three shelves 34 and a series of vertical dividers 36 dividing the interior of the housing 14 into 45-degree increments. FIG. 2 also show an embodiment of the housing 14 where the housing 14 has a center column substantially concentric to the cylinder to run wires and linkages through the assembly. In this embodiment, the top row of 45-degree increments is taller than the bottom row.

FIG. 4 shows the embodiment of FIG. 2 further comprising two trays 18, one on the top row, and one on the bottom row. In this embodiment, the trays 18 stick out beyond the shelves 34 to reduce the non-sterile surface exposed during surgery. The top row tray is a long tray 19 which is taller to accommodate robotic and laparoscopic instrument trays 18, while the bottom row tray is a short tray 17 which is shorter for ports and instrument trays 18.

In another embodiment, the center column may contain linkages such that when one foot pedal or touch screen button is pressed, the upper front-facing tray door 24 is opened, and when a different pedal or button is pressed, the lower front-facing tray 18 is opened. In another embodiment, motors may be used to open the upper-front facing tray 18, the lower front-facing tray 18, or each tray 18 individually.

In some embodiments of the present disclosure, the cart 10 further comprises a washing machine configured to wash medical instruments 22.

In some embodiments, the processor 28 is also in electrical communication with the second motor for translating the housing 14 along the longitudinal axis.

The processor 28 also has a user interface 32 for capturing user input. In one embodiment, the user interface 32 is an electronic touch screen.

Prior to a procedure, the cart 10 is loaded with required instruments along with necessary backups. Once loaded, the cart 10 keeps the instruments sterile until they are selected and opened by the nurse. During the procedure, a user selects a required instrument using the user interface 32. The first motor 16 rotates the housing 14 such that the tray 18 containing the instrument is facing the user. The door assembly open the door 24 of the tray 18. The retainer 20 may have a motor configured to move the tray 18 towards to user. In either case, the user may then retrieve the instrument from the cart 10. The processor 28 records the instrument retrieved on the storage medium 30. The cart 10 therefore keeps all unused instruments sterile during the procedure, and records all used instruments as unsterile.

Tracking Instruments

Tracking the instruments is an important part of the cart 10 because it will speed cleanup, preparation for surgery, and improve patient safety. As mentioned previously, the cart 10 will need a processor 28 and software that communicates with the cylinder and the user, most likely in the form of a computer or tablet. This computer or tablet attached to the car will track all instruments and control the rotation of the housing 14 and open select trays 18. Actual tray 18 selection can be done using foot pedals or touch screen.

Tracking software will be implemented to identify which trays 18 are holding which instruments. This can be done by programming the trays 18 with the instruments and only using it to hold those instruments. Alternatively, an identifying code for specific instruments could be designated, and the cart 10 could read this code off of instruments using bar codes, radio-frequency chips, electrical signals, or just by manual typed entry. The software should also track which instruments are "used", meaning the instruments have been exposed to the air during surgery because the door 24 has been opened. The software will used this information to generate a checklist which can be displayed to ensure the instruments are with the cart 10 and will be loaded back into the cart 10 after sterilization. The checklist can also be used to prevent retained instruments.

Another important aspect instrument tracking involves replacement of damaged or expired instruments. The tracking software can track the damage or expiration status of an instrument, as well as the lifetime remaining for disposable and limited-use instruments. Robotic instruments in particular have limited-use before they need to be replaced.

Additional Description of Exemplary Embodiments

The basic design is rolling cart that houses a rotating cylinder (aka, a "lazy Susan") that can be raised from within the cart (see FIG. 1). The cart may or may not have a built-in washer for washing the instruments contained in the trays. The housing has shelves for holding trays; the trays are designed to hold the sterile operating instruments. The cylinder and cart system has mechanisms that allow the trays to be opened with a foot pedal or using an electronic touchscreen. Additionally, this mechanism may enable the instruments to come out of the tray for easier and cleaner access by a nurse. Post-surgery, the instruments will need to be rinsed and cleaned. These instruments will then be put back into the trays, sterilized and loaded into the cylinder again. A computer system can be adapted to track and maintain a count of the instruments used.

Trays for the Instruments

The cart may be useful for storage of robotic tools. For a robotic surgery, a combination of open instruments (those used in open surgery), laparoscopic instruments, and robotic instruments may be used.

TABLE 1

Instruments used for smart cart.

| Part (or Parts) | Long or short | Quantity |
| --- | --- | --- |
| Robotic hook | Long | 1 |
| Robotic needle drivers | Long | 2 |
| Robotic bipolar | Long | 1 |
| Robotic scissors | Long | 1 |
| Laparoscopic suction | Long | 1 |
| Laparoscopic scissors | Long | 1 |
| Laparoscopic needle driver | Long | 1 |
| Laparoscopic grasper | Long | 1 |
| Laparoscopic hook | Long | 1 |
| Metallic ports | Short | 4 |
| Various open instruments | Short | 15-20 |

The instruments needed for an exemplary surgery are listed in Table 1. The cart may have two different sized trays to hold the long and short instruments efficiently (the longest instrument that could be included is 58.2 cm for the cart size used). For the robotic instruments, spares may be needed in case of broken or ineffective robotic instruments. To account for this, trays that can hold more than one instrument may also be needed.

Post-surgery, since the whole tray may be autoclaved, these will be exposed to high temperatures and steam (autoclaving requires temperatures of at least 121 degrees Celsius or 132 degrees Celsius), so all components used may have a sufficiently high storage (non-operating) rating. To avoid exposure to steam the electronics may be in a sealed case in the tray.

Another important concern is work flow, function, and storage. The trays may be loaded onto a cart that is going to be autoclaved, so they may have to be stackable, or at least lay flat easily, and preferably not weigh more than 25 pounds. While in the autoclave, steam should be able to penetrate the tray, and the contents must be able to dry during the drying cycle. There are many approaches to allow steam flow while limiting exposure to airborne pathogens, such as perforations, or air filters, or even valves. The trays should also be easy to pick up and move without injury, so handles might be a good addition.

Housing

In some embodiments, the housing is intended to hold the instrument trays during surgery and rotate to present the selected tool/tray to the nurse or other user. The cylinder's dimensions are dictated by the cart, and the cart is based on the dimensions of the back table currently used in surgery. Common widths of the back table are 24, 30, and 44 inches. Common lengths are 48, 60, and 92 inches. The height of the table is usually 34 inches, but can be 36 inches or more. Since the housing can be stored in the cart, the maximum height is dictated by the car, and has to be within the sterile field so cannot be too high. The radius of the cylinder may depend on the depth of the cart.

The trays may protrude from the housing to reduce the non-sterile surface exposed during surgery. The figures show 45 degree shelves, but other angles are possible.

FIG. 4 depicts an exemplary cylindrical housing. The embodiment showing includes three circular shelves each split up at 45 degree increments. This could be changed depending on the capacity requirements and number of surgeries the cart can be used for consecutively. There may be an interface between the trays and the cylinder so there is a space that wires and linkages can run through (the small hole in the center of the cylinder). The top row is taller to accommodate the robotic and laparoscopic instrument trays, while the bottom shelf is for the ports and open instrument trays.

A column of the housing may house linkages to open an upper or lower tray when actuated using, for example, a foot pedal, a touch screen, voice recognition, gesture control, etc. Alternatively if motors are used then there can be a motor for the top and bottom, or for each tray slot. Through the use of linkages and/or motors, motion in the cylindrical housing may be converted into motion of the tray through a back portion of the tray (e.g., a central column of the cylindrical housing). In addition, electronics inside the tray may need to be powered, and output data may be recorded via a computer, so an electrical connection may be made with all of the trays.

Tracking

Embodiments of the cart may also "know" which instruments are "used" (e.g., exposed to the air during surgery because the door has been opened). This may be used to generate a checklist that can be displayed to ensure all of the instruments are accounted for. This will make it much easier to ensure the instruments are with the cart and will be loaded back into the cart after they are sterilized. It also can be used to prevent retained instruments.

Another aspect of instrument tracking involves replacement of damaged, or expired instruments. Some embodiments of the cart, include a transceiver for communication between certain instruments and the cart for information such as, for example, an indication that an instrument is damaged. In this way, the instrument can be replaced by an appropriate support group. Robotic instruments in particular have limited use before they need to be replaced. There is a set number of surgeries that robotic instruments can be used for before they need to be replaced. All of this information will have to be easy to store and access so appropriate actions can be taken.

Sterile Concerns

The doors to the cart and the slots for the instruments may be considered noncritical, meaning they only come in contact with skin, and therefore only need to be decontaminated between surgeries. All of the instruments involved in surgery may be defined as critical because they come in contact with the inside of the patient, and therefore need to be sterile before entering surgery. Before they can be sterilized in an autoclave the instruments must be cleaned. Before they are cleaned the instruments need to be run under cold water. This removes most of the visible soil, and prevents any blood from drying. Cleaning can be done with an automated machine, depending on the instrument.

For robotic instruments to be cleaned, special steps are typically taken. The exterior may first be scrubbed with a soft brush to get rid of most of the visible soil. Water may then be run through the ports while moving the hinges through their full range of motion until the rinse water is clear. The ports may then be primed with a solution for cleaning, and then cleaned in an ultrasonic cleaner. After the ultrasonic cleaning, ports may be flushed with pressurized water. Then, compressed air may be run through the ports to remove remaining water. After removal of water with the compressed air, the instrument is lubricated. Lastly, the outside of the instrument is wiped with alcohol to be ready for sterilization. There are automated cleaners that perform most of these tasks, and some embodiments of the present cart may include such an automated cleaner. In this way, all of the instruments may be kept in a centralized location until the trays are filled and autoclaved.

Although the present disclosure has been described with respect to one or more particular embodiments, it will be understood that other embodiments of the present disclosure may be made without departing from the spirit and scope of the present disclosure. Hence, the present disclosure is deemed limited only by the appended claims and the reasonable interpretation thereof.

What is claimed is:

1. A cart for medical instruments, comprising:
  a housing having a longitudinal axis;
  a first motor configured to rotate the housing about the longitudinal axis; and
  one or more trays removably disposed within the housing, each tray having one or more retainers, each of the one or more retainers configured to hold a medical instrument, and wherein each tray includes a door;

an actuator configured to open the door; and a processor operably connected to the first motor, wherein the processor is programmed to:
- receive a request for a medical instrument;
- cause the first motor to rotate the housing until a tray containing the requested medical instrument is at a working position; and
- record a use of the requested medical instrument on a storage medium.

2. The cart of claim 1, wherein the actuator is a part of the tray such that each of the one or more trays include an actuator.

3. The cart of claim 1, wherein the actuator is a part of the housing and configured to cooperate with a door of a tray in the working position.

4. The cart of claim 1, wherein the actuator is a mechanical linkage actuated by manipulation of a user.

5. The cart of claim 1, wherein the actuator is an electric actuator.

6. The cart of claim 5, wherein the actuator is operably connected to the processor.

7. The cart of claim 1, further comprising a touch-sensitive display in electronic communication with the processor, and wherein the processor is further programmed to display a user interface on the display.

8. The cart of claim 1, wherein the housing further comprises one or more shelves to support the one or more trays.

9. The cart of claim 1, wherein the housing further comprises one or more vertical dividers for separating each tray of the one or more trays from others of the trays.

10. The cart of claim 1, wherein each tray includes a moveable platform to which the one or more retainers are affixed, and wherein the moveable platform is configured to move instruments held by the retainers to a user position when the door of the tray is opened.

11. The cart of claim 1, wherein the housing is substantially cylindrical.

12. The cart of claim 1, further comprising a second motor configured to translate the housing along the longitudinal axis.

* * * * *